United States Patent [19]

Kamiya et al.

[11] Patent Number: 5,354,842
[45] Date of Patent: Oct. 11, 1994

[54] METHOD FOR DETERMINING BRANCH DISTRIBUTION OF POLYMER

[75] Inventors: Tatsuyuki Kamiya, Kawasaki; Narumi Ishikawa, Nagareyama; Shigemitsu Kambe, Kawasaki, all of Japan

[73] Assignee: Nippon Petrochemicals Company, Ltd., Tokyo, Japan

[21] Appl. No.: 90,998

[22] Filed: Jul. 13, 1993

Related U.S. Application Data

[63] Continuation of Ser. No. 601,667, Oct. 23, 1990, abandoned.

Foreign Application Priority Data

Oct. 31, 1989 [JP] Japan .................................. 1-281852

[51] Int. Cl.$^5$ ........................ C08F 6/26; C08F 210/16
[52] U.S. Cl. ................................ 528/503; 526/348; 526/352; 526/352.2
[58] Field of Search .............. 528/503; 526/352, 352.2

[56] References Cited

U.S. PATENT DOCUMENTS 4,668,752  5/1987  Tominari ........................ 526/348.2

OTHER PUBLICATIONS

P. J. Flory, Trans. Farad. Soc., 51, 848 (1955).
J. Varga, J. Thermal Anal., 10 (1976) 433–440.

*Primary Examiner*—Fred Zitomer
*Attorney, Agent, or Firm*—Dilworth & Barrese

[57] ABSTRACT

A branch distribution of a crystalline polymer is determined by melting the polymer at a temperature sufficiently higher than the melting point thereof, then cooling the melted polymer to room temperature in such a manner that isothermal crystallization of the polymer is allowed to take place stepwise at intervals of 3° C. or higher at least from near the upper limit of the melting point of the polymer, then raising the temperature to melt the crystals and determining a branch distribution from the melt behavior, using a thermal analyzer.

12 Claims, No Drawings

METHOD FOR DETERMINING BRANCH DISTRIBUTION OF POLYMER

This is a continuation of copending application Ser. No. 07/601,667 filed on Oct. 23, 1990, now abandoned.

BACKGROUND OF THE INVENTION

The present invention relates to a method for determining a branch distribution of a crystalline polymer and more particularly to a method for determining a branch distribution of a crystalline polymer on the basis of a melt behavior of the polymer in which the polymer is stepwise crystallized isothermally and thereafter melted, using a thermal analyzer.

PRIOR ART

It is known that in the case of a polymer containing a branch distribution, particularly a polyolefin resin or a composition thereof, the branch distribution thereof exerts a great influence on product physical properties. Especially, in the case of linear low-density polyethylene (LLDPE), its branch distribution exerts a serious influence on the heat selability or transparency of films formed therefrom or on the stress cracking resistance of pipes or the like formed therefrom, so various methods for determining a branch distribution are now under study.

According to a branch distribution determining method which is used at present, each of components obtained by molecular weight fractionation is determined for an average branch density using NMR or an infrared spectrophotometer. By this method, however, only a branch density in each of certain molecular weight ranges can be determined, and no information is provided about the branch distribution in the whole of a composition.

As a branch distribution determining method which has solved the above-mentioned problem there is known a temperature rising elution fractionation (TREF) method. This method utilizes the fact that the solubility of a crystalline polymer in a solvent depends on a branch density, and this method has been studied as a method for structural analysis of LLDPE. A more detailed structural analysis is also being made by the combination of the foregoing molecular weight fractionation and TREF method.

However, the TREF method requires special apparatus and skill, and a long time of 15 to 20 hours is required for the determination, including pretreatment, so it is difficult to apply the TREF method to the quality control in a commercial plant for example.

On the other hand, Paul J. Flory has published a theory of equilibrium melting point drop based on a copolymer composition [Trans. Farad. Soc:, 51, 848 (1955)]. According to this theory, as the density of amorphous units contained in a crystalline polymer chain increases, an equilibrium melting point drops linearly. The "amorphous units" as referred to herein indicate short-chain branches formed by an $\alpha$-olefin copolymerized with ethylene. According to this theory, if a crystalline polymer is crystallized stepwise thermodynamically under conditions close to equilibrium crystallization, it can be crystallized (segregation) at each of various branch densities. And if the crystalline polymer thus crystallized is melted stepwise, there ought to be obtained a melting heat chart corresponding to the branch densities. It is expected that by using the said chart there will be obtained information on a branch distribution.

It is reported in literatures [see, for example, Journal of Thermal Analysis, Vol.10, pp.433–440 (1976)] that if a crystalline polymer containing a branch structure is crystallized and then melted while the temperature is dropped stepwise using a thermal analyzer, the process of the crystallization is memorized as it is and is reflected in the melt behavior. It is presumed that the cause of this phenomenon has a bearing on the branch distribution.

Thus, although it is suggested that the branch distribution of a crystalline polymer and the crystallization or the melt behavior have a close relation to each other, a method of clarifying the relation of the two and utilizing it concretely in the analysis of branch distribution has not been known.

SUMMARY OF THE INVENTION

It is the object of the present invention to provide a method for determining a branch distribution of a polymer in a simple manner, in a short time, with an accuracy equal to that of the TREP method, using the Flory theory and without using any special apparatus.

Having made extensive studies with respect to the above-mentioned object, the present inventors have discovered that a correlation of high accuracy is obtained between the melt behavior and the branch distribution of a polymer by isothermal crystallization and subsequent melting of the polymer stepwise at intervals of a certain temperature or higher using a thermal analyzer.

The present invention resides in a method for determining a branch distribution of a crystalline polymer which method comprises, using a thermal analyzer, melting the polymer at a temperature sufficiently higher than the melting point thereof, then cooling the melted polymer to room temperature in such a manner that isothermal crystallization of the polymer is allowed to take place stepwise at intervals of 3° C. or higher at least from near the upper limit of the melting point of the polymer, then raising the temperature to melt the crystals and determining a branch distribution from the melt behavior.

DETAILED DESCRIPTION OF THE INVENTION

The contents of the present invention will be described in detail hereinunder.

Examples of the crystalline polymer whose branch distribution can be determined by the present invention include all polymers containing a crystalline portion, particularly polyolefins. Further, the method of the present invention is particularly effective for polyolefins of a structure having short chains on a straight-chain portion, e.g. LLDPE, because it is important in studying the relation of branch distribution to the physical properties of such polymers.

The thermal analyzer used in the present invention used may be used a conventional differential scanning calorimeter (DSC) or differential thermal analyzer (DTA). It is desirable to use a thermal analyzer which is high in sensitivity and ensures a stable temperature control. From the standpoint of determination efficiency it is desirable to use a thermal analyzer which permits an automatic temperature control.

In the determination method of the present invention, crystallizing a polymer continuously from near the melting point of the polymer over as long a time as possible according to the Flory's theory is considered most suitable accuracy because it is possible to determine branch densities in a continuous manner. On the other hand, however, at the time of melting it is necessary to detect the difference from a standard substance in view of the principle of the thermal analyzer, so it is necessary to maintain a rate of temperature increase at a certain value or higher. At the time of melting, therefore, there arises a delay of melting due to the phenomenon of superheating, thus resulting in a certain unavoidable deterioration of the resolving power. Having made studies about optimal conditions while taking both these inconsistent points into account, the present inventors found out that by allowing isothermal crystallization to take place stepwise at intervals of 3° C. or more before determination of the melt behavior using a thermal analyzer there can be determined a branch distribution to a satisfactory extent despite of the superheating phenomenon during melting. If this interval is less than 3° C., the separation of peaks on a melt behavior determination chart becomes incomplete and it is no longer possible to effect a highly accurate determination. Where a branch distribution is to be determined with high accuracy, it is preferable that the interval be 3° C. or more and as close as possible to 3° C. But this interval may be increased according to the object of the determination. Usually, there is used a certain interval in the range of 3° to 10° C.

For determining a branch distribution from the melt behavior obtained it is necessary to determine a melting point of a sample whose branch density is known and in a narrow range by the method of the present invention and obtain a correlation between the melting point and the branch density to be used in the present invention. Since an isothermal crystallization temperature corresponding to the melting point can be obtained easily, there also can be easily obtained a correlation between such isothermal crystallization temperature and the branch density. Either of these correlations may be used in the analysis.

Further, by measuring a melting heat value of a sample having a known branch distribution of a narrow range, it is possible to determine a crystallinity corresponding to each branch density on the basis of the measured value and a melting heat value (287.6 J/g) of a perfect crystal polyethylene. Then, by analyzing a melting heat chart obtained according to the method of the present invention using the crystallinity values thus obtained, it is possible to calculate the content of each section corresponding to each branch density.

By practicing the present invention using the above method it is possible to determine a branch distribution extremely easily.

As to the duration of each isothermal crystallization step, it is desirable to use a long time for each step to come as close as possible to an equilibrium state, but a duration of not longer than 200 minutes is suitable in consideration of shortening of the total time required for the determination. Further, the lower the temperature, the more rapidly the crystallization proceeds, so by shortening the duration of each stage successively with the shift from a high temperature stage to a lower temperature stage, it is possible to further shorten the determination time without great deterioration of accuracy.

By practicing the present invention there can be obtained results almost equal to the results obtained by the TREF method with respect to the branch distribution of a crystalline polymer, in a much simpler manner and in a short time of several hours to 10 hours or so. Therefore, the method of the present invention can be employed as the quality control for a manufacturing process in a commercial plant.

WORKING EXAMPLE AND COMPARATIVE EXAMPLE

The present invention will be described below concretely in terms of working and comparative examples, but the invention is not limited thereto.

EXAMPLE

An ethylene-1-butene copolymer was divided into sections almost uniform in branch density by the TREF method and then each section was subjected to the determination by the DSC method according to the present invention to obtain a correlation of branch density and crystallization temperature. The branch density was determined using $^{13}$CNMR. The results are as shown in Table 1.

TABLE 1

| Isothermal Crystallization Temperature (°C.) | Branch Density (ethyl group/1,000 C) |
| --- | --- |
| 131 | — |
| 126 | 0–3 |
| 121 | 3–7 |
| 116 | 7–11 |
| 111 | 11–16 |
| 106 | 16–20 |
| 101 | 20–24 |

Next, an ethylene-1- butene copolymer as a sample was melted sufficiently at 200° C. and thereafter subjected to isothermal crystallization in accordance with the program shown in Table 2.

TABLE 2

| Set Temperature (°C.) | Temperature Dropping Rate (°C./min) | Isothermal Crystallization Time (min) |
| --- | --- | --- |
| 200 | | |
| ↓ | 10 | |
| 136 | | 0 |
| ↓ | 0.5 | |
| 131 | | 120 |
| ↓ | 0.5 | |
| 126 | | 90 |
| ↓ | 0.5 | |
| 121 | | 80 |
| ↓ | 0.5 | |
| 116 | | 70 |
| ↓ | 0.5 | |
| 111 | | 50 |
| ↓ | 0.5 | |
| 106 | | 30 |
| ↓ | 0.5 | |
| 101 | | 20 |
| ↓ | 5 | |
| 20 | | 15 |
| | | Total 475 min |

After completion of the isothermal crystallization, the copolymer was melted by heating at a rate of 5° C./min up to 200° C. and there was obtained a temperature-melting heat value relation. An isothermal crystallization temperature corresponding to each melting peak was obtained by comparing the melt behavior with the behavior of crystallization, and from the results obtained there were determined branch densities corresponding to the peaks, using the measured values shown in Table 1.

Further, on the basis of the above results the content of each section corresponding to each branch density was determined according to the foregoing method. The results are set forth in Table 3 together with the results of the determination made on the same sample by the TREF method. The content of a section corresponding to a branch density of 0-24 ethyl group/1,000 C was assumed to be 100 wt %.

TABLE 3

| Branch Density (ethyl group/1,000 C) | DSC Method According to the Present Invention (wt %) | TREF Method (wt %) |
|---|---|---|
| 0-3 | 23 | 22 |
| 3-7 | 29 | 27 |
| 7-11 | 17 | 19 |
| 11-16 | 12 | 13 |
| 16-20 | 10 | 11 |
| 20-24 | 9 | 8 |

As is seen from the above results, the time required for the isothermal crystallization is about 8 hours, which is not longer than one half of the time required in the conventional TREF method. In addition, the result of the determination of a branch distribution was in good coincidence with the result obtained by the TREF method.

What is claimed is:

1. A method for determining a branch distribution of a crystalline polymer, which method comprises, melting the polymer using a differential scanning calorimeter or differential thermal analyzer, then cooling the melted polymer to room temperature in such a manner that isothermal crystallization of the polymer is allowed to take place stepwise at intervals of from 3° to 10° C. at least from about the highest melting point of the polymer, then melting the crystals;

providing a correlation chart of crystallization temperatures for polymer samples having known branch densities; and comparing the melt behavior of the crystalline polymer with the crystallization temperatures contained in the correlation chart to determine a branch distribution from the melt behavior.

2. A method as set forth in claim 1, wherein said crystalline polymer is a polyolefin.

3. A method as set forth in claim 2, wherein said polyolefin is a polyethylene.

4. A method as set forth in claim 3, wherein said polyethylene is a ethylene-α-olefin copolymer.

5. A method as set forth in claim 4, wherein said ethylene-α-olefin copolymer is a linear low-density polyethylene.

6. A method for determining a branch distribution of a crystalline polymer, which method comprises, melting the polymer using a differential scanning calorimeter or differential thermal analyzer, then cooling the melted polymer to room temperature in such a manner that isothermal crystallization of the polymer is allowed to take place stepwise at intervals of from 3° to 10° C. at least from about the highest melting point of the polymer, the duration of the isothermal crystallization in each isothermal crystallization stage being not longer than 200 minutes, and said duration of each isothermal crystallization stage being shorter than the previous stage, then melting the crystals and determining a branch distribution for the melt behavior.

7. A method as set forth in claim 1 wherein the duration of the isothermal crystallization in each isothermal crystallization stage is not longer than 200 minutes.

8. A method as set forth in claim 7 wherein the duration of each isothermal crystallization stage is shorter than the previous isothermal crystallization stage.

9. A method for determining a branch distribution of a crystalline polymer, which method comprises:

providing a crystalline polyolefin of a structure having side chains of a specific number of carbon atoms;

melting the polymer, using a differential scanning calorimeter or differential thermal analyzer;

then cooling the melted polymer to room temperature in such a manner that isothermal crystallization of the polymer is allowed to take place stepwise at intervals of from 3° to 10° C. at least from about the highest melting point of the polymer, the duration of the isothermal crystallization in each isothermal crystallization stage being not longer than 200 minutes;

then melting the crystals; and determining a branch distribution from the melt behavior.

10. A method as in claim 9 wherein determining branch distribution comprises providing a correlation chart of crystallization temperatures for polymer samples having known branch densities; and comparing the melt behavior of the crystalline polymer with the crystallization temperatures contained in the correlation chart.

11. A method as in claim 9 wherein the duration of each isothermal crystallization stage is shorter than the previous isothermal crystallization stage.

12. A method as in claim 9 wherein said crystalline polymer is a linear low-density polyethylene.

* * * * *